(12) United States Patent
Hossainy et al.

(10) Patent No.: US 8,591,934 B2
(45) Date of Patent: *Nov. 26, 2013

(54) COATINGS OF ACRYLAMIDE-BASED COPOLYMERS

(71) Applicant: Abbott Cardiovascular Systems Inc., Santa Clara, CA (US)

(72) Inventors: Syed Faiyaz Ahmed Hossainy, Hayward, CA (US); Thierry Glauser, Redwood City, CA (US); Mikael O. Trollsas, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/677,115

(22) Filed: Nov. 14, 2012

(65) Prior Publication Data

US 2013/0071449 A1 Mar. 21, 2013

Related U.S. Application Data

(63) Continuation of application No. 13/206,417, filed on Aug. 9, 2011, now Pat. No. 8,333,984, which is a continuation of application No. 11/639,860, filed on Dec. 15, 2006, now Pat. No. 8,017,141.

(51) Int. Cl.
*A61F 2/00* (2006.01)

(52) U.S. Cl.
USPC .......................................... 424/423; 424/422

(58) Field of Classification Search
None
See application file for complete search history.

(56) References Cited

U.S. PATENT DOCUMENTS

| | | | |
|---|---|---|---|
| 3,893,988 A | 7/1975 | Seymour et al. |
| 4,931,287 A | 6/1990 | Bae et al. |
| 5,019,096 A | 5/1991 | Fox, Jr. et al. |
| 5,163,952 A | 11/1992 | Froix |
| 5,258,020 A | 11/1993 | Froix |
| 5,607,467 A | 3/1997 | Froix |
| 5,616,338 A | 4/1997 | Fox, Jr. et al. |
| 5,674,242 A | 10/1997 | Phan et al. |
| 5,723,219 A | 3/1998 | Kolluri et al. |
| 5,824,049 A | 10/1998 | Ragheb et al. |
| 5,873,904 A | 2/1999 | Ragheb et al. |
| 5,879,713 A | 3/1999 | Roth et al. |
| 5,932,299 A | 8/1999 | Katoot |
| 5,962,138 A | 10/1999 | Kolluri et al. |
| 5,997,517 A | 12/1999 | Whitbourne |
| 6,096,070 A | 8/2000 | Ragheb et al. |
| 6,110,483 A | 8/2000 | Whitbourne et al. |
| 6,143,354 A | 11/2000 | Koulik et al. |
| 6,159,978 A | 12/2000 | Myers et al. |
| 6,180,632 B1 | 1/2001 | Myers et al. |
| 6,214,901 B1 | 4/2001 | Chudzik et al. |
| 6,245,760 B1 | 6/2001 | He et al. |
| 6,248,129 B1 | 6/2001 | Froix |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,299,604 B1 | 10/2001 | Ragheb et al. |
| 6,306,176 B1 | 10/2001 | Whitbourne |
| 6,344,035 B1 | 2/2002 | Chudzik et al. |
| 6,383,196 B1 | 5/2002 | Bates et al. |
| 6,387,379 B1 | 5/2002 | Goldberg et al. |
| 6,475,779 B2 | 11/2002 | Mathiowitz et al. |
| 6,482,834 B2 | 11/2002 | Spada et al. |
| 6,524,347 B1 | 2/2003 | Myers et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,613,432 B2 | 9/2003 | Zamora et al. |
| 6,620,617 B2 | 9/2003 | Mathiowitz et al. |
| 6,663,662 B2 | 12/2003 | Pacetti et al. |
| 6,730,064 B2 | 5/2004 | Ragheb et al. |
| 6,776,796 B2 | 8/2004 | Falotico et al. |
| 6,790,228 B2 | 9/2004 | Hossainy et al. |
| 6,890,583 B2 | 5/2005 | Chudzik et al. |
| 7,005,137 B1 | 2/2006 | Hossainy et al. |
| 7,008,667 B2 | 3/2006 | Chudzik et al. |
| 7,077,859 B2 | 7/2006 | Sirhan et al. |
| 7,094,256 B1 | 8/2006 | Shah et al. |
| 7,217,426 B1 | 5/2007 | Hossainy |
| 7,396,539 B1 | 7/2008 | Hossainy et al. |
| 7,560,492 B1 | 7/2009 | Claude et al. |
| 7,563,454 B1 | 7/2009 | Pacetti |
| 2001/0007083 A1 | 7/2001 | Roorda |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0082679 A1 | 6/2002 | Sirhan et al. |
| 2002/0111590 A1 | 8/2002 | Davila et al. |
| 2002/0165608 A1 | 11/2002 | Llanos et al. |
| 2002/0176849 A1 | 11/2002 | Slepian |
| 2002/0188037 A1 | 12/2002 | Chudzik et al. |
| 2003/0004141 A1 | 1/2003 | Brown |
| 2003/0028243 A1 | 2/2003 | Bates et al. |

(Continued)

FOREIGN PATENT DOCUMENTS

| | | |
|---|---|---|
| WO | WO 96/15157 | 5/1996 |
| WO | WO 98/01478 | 1/1998 |
| WO | WO 2005/007798 | 1/2005 |

OTHER PUBLICATIONS

U.S. Appl. No. 13/470,073, filed May 11, 2012, Ding et al.
International Search Report for PCT/US2007/087300, mailed Jun. 17, 2008, 15 pgs.
Chang et al., "Surface-attached polymer monolayers for the control of endothelial cell adhesion", Physicochemical and Engineering Aspects 198-200, pp. 519-526, 2002.
Chiefari et al., "Living Free-Radical Polymerization by Reversible Addition-Fragmentation Chain Transfer: The RAFT Process", Macromolecules 31, pp. 5559-5562, 1998.

(Continued)

*Primary Examiner* — James Rogers
(74) *Attorney, Agent, or Firm* — Squire Sanders (US) LLP

(57) ABSTRACT

An implantable device including a conjugate formed of an acrylamide-based copolymer and a bioactive agent is provided.

26 Claims, No Drawings

(56) References Cited

U.S. PATENT DOCUMENTS

| | | |
|---|---|---|
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0060877 A1 | 3/2003 | Falotico et al. |
| 2003/0065377 A1 | 4/2003 | Davila et al. |
| 2003/0083739 A1 | 5/2003 | Cafferata |
| 2004/0063805 A1 | 4/2004 | Hossainy et al. |
| 2005/0070936 A1 | 3/2005 | Pacetti |
| 2005/0106203 A1 | 5/2005 | Roorda et al. |
| 2005/0266038 A1 | 12/2005 | Glauser et al. |

OTHER PUBLICATIONS

Damink et al., "Cross-linking of dermal sheep collagen using a water-soluble carbodiinide", Biomaterials vol. 17, No. 8, pp. 765-773, 1996.

Hausmann et al., "Novel Functionalised Ethylene Acrylate Copolymers as Polymer Modifiers", Paper presented at Addcon World 2003, 7 pgs.

http://www.merckmanuals.com/professional/pulmonary_disorders/tumors_of_the_lungs/lung_carcinoma.html.

Kamigaito et al., "Metal-Catalyzed Living Radical Polymerization", Chem. Rev. 101, pp. 6389-3745, 2001.

Kopeček et al., "Water soluble polymers in tumor targeted delivery", J. of Controlled Release 74, pp. 147-158 (2001).

Krstina et al., "Narrow Polydispersity Block Copolymers by Free-Radical Polymerization in the Presence of Macromonomers", Macromolecules 28, pp. 5381-5385, 1995.

Matyjaszewski et al., "Atom Transfer Radical Polymerization", Chem. Rev. 101, pp. 2921-2990, 2001.

Odian, Principles of Polymerization, John Wiley & Sons, $3^{rd}$ Ed. pp. 142-145 (1993).

Patten et al., "Atom Transfer Radical Polymerization and the Synthesis of Polymeric Materials", Adv. Mater. 10, No. 12, pp. 901-915, 1998.

Peterson et al., "HPMA Copolymer Delivery of Chemotherapy and Photodynamic Therapy in Ovarian Cancer", Ed. by Maeda et al., pp. 101-123, 2003.

Řihova et al., "Doxorubicin bound to a HPMA copolymer carrier through hydrazone bond is effective also in a cancer cell line with a limited content of lysosomes", J. of Controlled Release 74, pp. 225-232 (2001).

Řihová et al., "Drug-HPMA-HuIg Conjugates Effective Against Human Solid Cancer", Ed. by Maeda et al., pp. 125-143, 2003.

COATINGS OF ACRYLAMIDE-BASED COPOLYMERS

CROSS-REFERENCE TO RELATED APPLICATIONS

This application is a continuation of application Ser. No. 13/206,417, filed Aug. 9, 2011, which is and which is a continuation of application Ser. No. 11/639,860, filed Dec. 15, 2006, now U.S. Pat. No. 8,017,141, each of which are incorporated herein by reference.

FIELD OF THE INVENTION

This invention generally relates to acrylamide-based copolymers for coating an implantable device such as a drug delivery stent.

DESCRIPTION OF THE BACKGROUND

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

The existing polymeric coating on a stent can have different types of limitations. For example, some poly(ester amide) based coatings can have poor mechanical properties so as to compromise coating integrity, and coating based on hydrophobic polymers can have problems in controlling release of a hydrophilic drug.

Therefore, there is a need for new carrier materials for controlled delivery of an agent.

The polymer and methods of making the polymer disclosed herein address the above described problems.

SUMMARY OF THE INVENTION

Poly(HPMA) is a hydrophilic polymer which has been used to conjugate a bioactive agents such as drugs, peptides and proteins. This conjugation can lead to increased circulation time in the bloodstream of these bioactive agents as well as these agents' uptake by the cellular endoplasm (Ulbrich K., et al., Advance in Experimental Medicine and Biology: Polymer Drugs in the Clinical Stage, 519:125-143 (2003).

Accordingly, provided in this invention is a coating on an implantable device, the coating comprising a acrylamide-based copolymer that can conjugate to a bioactive agent. The polymer can have a chosen degree of hydrophilicity by virtue of the presence of the hydroxy groups on the polymer backbone. The coating can have a topcoat or a drug matrix that includes the acrylamide-based copolymer described herein. In some embodiments, the acrylamide-based copolymer includes poly[N-(2-hydroxypropyl)methacrylamide] (poly(HPMA)).

The bioactive active agent can be conjugated to the acrylamide-based copolymer via a labile linker. The bioactive agent can be conjugated to the polymer by conjugation to functional groups (e.g., hydrophilic groups) on the copolymer. In some embodiments, the bioactive agent can be conjugated to the acrylamide-based copolymer via hydrophilic groups on the acrylamide-based copolymer.

The bioactive agents can be any drugs, peptides, proteins, or combinations thereof. Some examples of the bioactive agent include, but are not limited to, halofuginone, paclitaxel, docetaxel, estradiol, nitric oxide donors, super oxide dismutases, super oxide dismutases mimics, 4-amino-2,2,6,6-tetramethylpiperidine-1-oxyl(4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, mometasone, bioactive RGD, CD-34 antibody, abciximab (REOPRO), progenitor cell capturing antibody, prohealing drugs, prodrugs thereof, co-drugs thereof, or a combination thereof.

An implantable device having a coating described herein can be used to treat, prevent, or ameliorate a vascular medical condition. Some exemplary vascular medical conditions include atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, and combinations thereof. For example, the implantable device can be planted within a tissue of a human being, e.g., in the blood vessel.

In some embodiments, the present invention provides a method of forming a coating on the implantable device. The method comprises
  providing a copolymer that comprises units derived from at least one acrylamide monomer,
  providing a bioactive agent,
  forming a conjugate of the bioactive agent and the copolymer, and
  forming a coating comprising the conjugate on the implantable device.

DETAILED DESCRIPTION OF THE INVENTION

Poly[N-(2-hydroxypropyl)methacrylamide] (Poly(HPMA)) is a hydrophilic polymer which has been used to conjugate a bioactive agents such as drugs, peptides and proteins. This conjugation can lead to increased circulation time in the bloodstream of these bioactive agents as well as these agents' uptake by the cellular endoplasm (Ulbrich K., et al., Advance in Experimental Medicine and Biology: Polymer Drugs in the Clinical Stage, 519:125-143 (2003).

Accordingly, provided in this invention is a coating on an implantable device, the coating comprising a acrylamide-based copolymer that can conjugate to a bioactive agent. The polymer can have a chosen degree of hydrophilicity by virtue of the presence of the hydroxy groups on the polymer backbone. The coating can have a topcoat or a drug matrix that includes the acrylamide-based copolymer described herein. In some embodiments, the acrylamide-based copolymer includes poly(HPMA).

The bioactive active agent can be conjugated to the acrylamide-based copolymer via a labile linker. The bioactive agent can be conjugated to the polymer by conjugation to functional groups (e.g., hydrophilic groups) on the copolymer. In some embodiments, the bioactive agent can be conjugated to the acrylamide-based copolymer via hydrophilic groups on the acrylamide-based copolymer.

The bioactive agents can be any drugs, peptides, proteins, or combinations thereof. Some examples of the bioactive agent include, but are not limited to, halofuginone, paclitaxel, docetaxel, estradiol, nitric oxide donors, super oxide dismutases, super oxide dismutases mimics, 4-amino-2,2,6,6-tetramethylpiperidine-1-oxyl(4-amino-TEMPO), tacrolimus, dexamethasone, rapamycin, rapamycin derivatives, 40-O-(2-hydroxy)ethyl-rapamycin (everolimus), 40-O-(3-hydroxy) propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, mometasone, bioactive RGD, CD-34 antibody, abciximab (REOPRO), progenitor cell capturing antibody, prohealing drugs, prodrugs thereof, co-drugs thereof, or a combination thereof.

An implantable device having a coating described herein can be used to treat, prevent, or ameliorate a vascular medical condition. Some exemplary vascular medical conditions include atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, and combinations thereof. For example, the implantable device can be planted within a tissue of a human being, e.g., in the blood vessel.

In some embodiments, the present invention provides a method of forming a coating on the implantable device. The method comprises
  providing a copolymer that comprises units derived from at least one acrylamide monomer,
  providing a bioactive agent,
  forming a conjugate of the bioactive agent and the copolymer, and
  forming a coating comprising the conjugate on the implantable device.

Acrylamide-Based Copolymer

The acrylamide-based copolymer can be formed of an acrylamide or methacrylamide monomer having a hydrophilic group. Preferably, the hydrophilic group is —OH, —SH, —NRH, —COOH, —COO⁻Na⁺, or —COO⁻K⁺.

In some embodiments, the acrylamide monomer forming the acrylamide-based copolymer can be an acrylamide or methacrylamide having the structure of formula I:

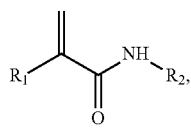

Formula I wherein $R_1$ is $CH_3$ or H, and $R_2$ can be any group having at least one hydroxyl, thiol, amino or carboxyl group. Examples of $R_2$ can be short chain hydroxyalkyl groups, a peptide sequence, an alkyl chain, or a linker.

The acrylamide-based copolymer can have different molar ratios of monomers. Such molar ratios of monomers can be designated as n and m. These molar ratios can independently range from about 0.01 to about 0.99 and the total values of molar ratios n+m=1. Some examples of the molar ratios are about 0.05, about 0.1, about 0.2, about 0.3, about 0.4, about 0.5, about 0.6, about 0.7, about 0.8, about 0.9, or about 0.95. Note, molar ratios of the monomers can affect the hydrophobicity of the copolymer. A higher ratio of hydrophobic monomers can result in a more hydrophobic copolymer, and vice versa. The hydrophobic nature of the copolymer can influence the release of a drug embedded, admixed, dissolved, or otherwise included in a matrix or coating including the copolymer.

The acrylamide-based copolymer can be formed by any established method of polymerization (see, e.g., Polymer Handbook, by Eric A. Grulke, Akihiro Abe, Daniel R. Bloch, and J. Brandrup (Eds), J&W Wiley, 2003). For example, the acrylamide-based copolymer can be formed by standard free radical copolymerization and controlled radical polymerization such as ATRP (T. E. Patten and K. Matyjaszewski, Adv. Mater. 10, (1998) pp. 901; K. Matyjaszewski and J. Xia, Chem. Rev. 101 (2001) pp. 2921; M. Kamigaito, T. Audo and M. Sawamoto Chem. Rev. 101 (2001) pp. 3689. and RAFT (reversible addition-fragmentation chain transfer) J. Krstina et al., Macromolecules 28 (1995) pp. 5381; G. Moad et al., WO 96/15157 (1996); T. P. Le et al., WO 9801478/A1 (1998); J. Chiefari et al., Macromolecules 31 (1998) pp. 5559 The polymerization or copolymerization can be carried out sequentially to yield a block copolymer of concurrently to yield a random copolymer, depending on the desired properties of the copolymer. A general scheme of forming the acrylamide-based copolymer is shown in Scheme I:

Scheme I

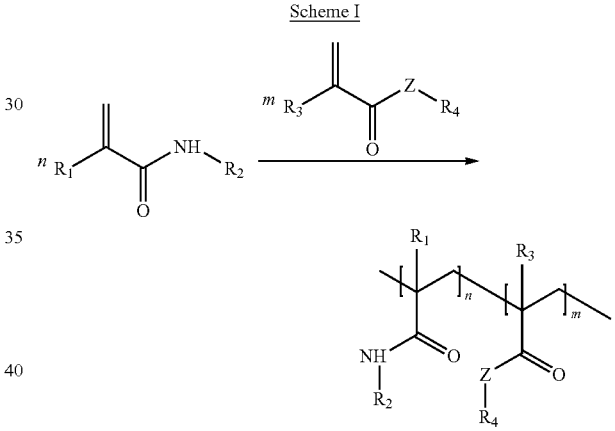

In Scheme I, $R_1$ and $R_2$ are defined as those in Formula I. $R_3$ is $CH_3$ or H. $R_4$ is a straight or branched C1-C12 alkyl, aryl, cycloalkyl, or heterocyclic group. $R_4$ can bear functional groups such as hydroxyl, alkoxy such as methoxy or ethoxy, thiol, carboxyl, NH, or other groups. Some examples of $R_4$ are $CH_3$, ethyl, propyl, 2-hydroxyethyl, butyl, or methoxyethyl. N and m are molar ratios of the two monomers and are independently from about 0.01 to about 0.99 and the total values of molar ratios n+m=1. Some examples of n and m are about 0.05, about 0.1, about 0.2, about 0.3, about 0.4, about 0.5, about 0.6, about 0.7, about 0.8, about 0.9, or about 0.95. Z can be O or NH.

In some embodiments, the acrylamide monomer is N-(2-hydroxy propyl)methacrylamide (HPMA). HPMA can easily polymerize alone or copolymerize with other monomers such as acrylamide, acrylate or methacrylate monomers to form a HPMA copolymer. Therefore, HPMA can be used as a monomer to introduce a chosen degree of hydrophilicity into the backbone of the acrylamide-based copolymer by forming a copolymer(s) with other monomers. A general scheme forming the HPMA copolymer can be illustrated by the reaction in Scheme II below:

Scheme II

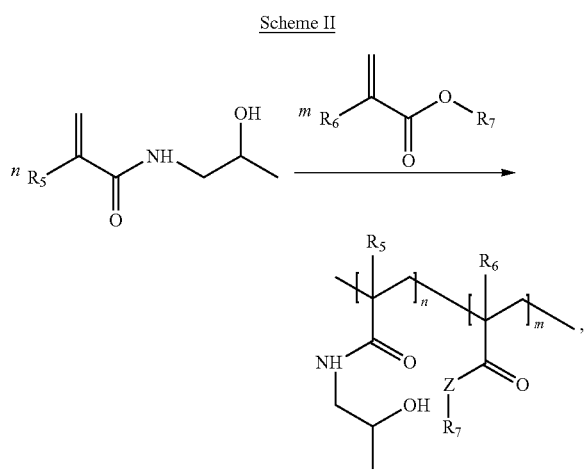

forming a HPMA-based copolymer having the general formula II

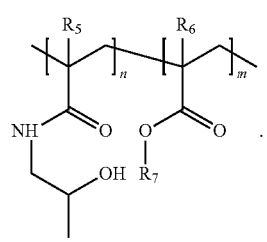

Formula II

In Scheme II and Formula II, n and m are molar ratios of the two monomers forming the copolymer and can independently range from about 0.01 to about 0.99. Some examples of n and m values are about 0.05, about 0.1, about 0.2, about 0.3, about 0.4, about 0.5, about 0.6, about 0.7, about 0.8, about 0.9, or about 0.95. $R_5$ and $R_6$ are independently $CH_3$ and H. $R_7$ is a straight or branched C1-C12 alkyl, aryl, cycloalkyl, or heterocyclic group. $R_7$ can bear functional groups such as hydroxyl, alkoxy such as methoxy or ethoxy, thiol, carboxyl, NH, or other groups. Some examples of $R_7$ are $CH_3$, ethyl, propyl, 2-hydroxyethyl, butyl, or methoxyethyl. An example of the HPMA-based copolymer of formula II is where $R_5$ and $R_6$ are $CH_3$, and $R_7$ is methoxyethyl. This polymer is poly[N-(2-hydroxypropyl)methacrylamide-co-methoxyethyl methacrylate] (HPMA-co-MOEMA), which can be a random or block copolymer.

Linkers

Any biocompatible linker can be used to conjugate a bioactive agent to the hydrophilic group on a monomer forming the poly(HPMA)-based polymer or on the poly(HPMA)-based polymer itself. In some embodiments, the linker can be any linker having about 40 atoms or less. In some embodiments, the linker can include poly(ethylene glycol) (PEG), poly(alkylene oxide), C1-C12 short chain alkyl, C1-C12 short chain cycloalkyl, C1-C12 aryl, peptide, protein, oligomer of amino acids or combinations thereof. In some embodiments, the linker is a labile linker. For example, such labile linker can include, e.g., a peptide sequence such as glycine-phenylalinine-leucine-glycine. Some other labile linkers include, but are not limited to, succinic anhydride, glutaric anhydride, dimethyl succinic anhydride, methyl glutaric anhydride, thioesters, disulfide bonds, PLA-, PLGA-, PCL-oligomers and other ester and anhydride linkages.

In some embodiments, the linker can include a vinyl group and can polymerize with HPMA or other monomers forming a poly(HPMA)-based copolymer having pendant linker molecules. The linker includes a free hydrophilic group (e.g., OH) for conjugation to a bioactive agent. Scheme III shows the formation of an example of a linker having PEG and a methacrylate group.

Scheme III

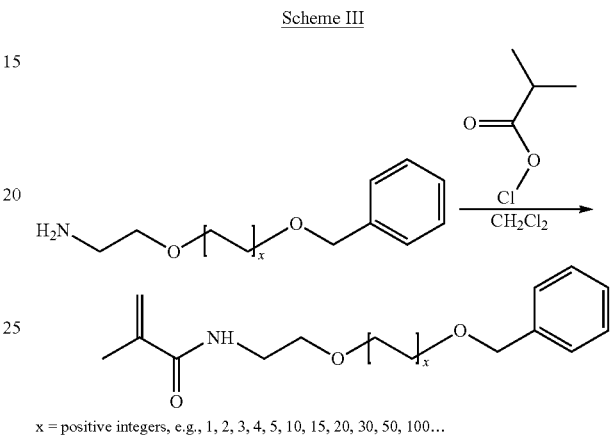

x = positive integers, e.g., 1, 2, 3, 4, 5, 10, 15, 20, 30, 50, 100...

As shown in Scheme III, a linker, such as PEG, a peptide sequence or an alkyl chain, can include two functional groups (e.g., a free amine, hydroxyl, thiol, carboxyl), one functional group being reactive and the other one being protected by a protective group such as benzyl group. The reactive group can react with a reactive vinyl group (e.g., acryloyl halide or methacryloyl halide) to form a vinyl group terminated PEG. The protective group can subsequently be removed by a process such as hydrogenation ($H_2$ gas and Pd/C) to yield a free functional group. This linker vinyl molecule with a reactive terminal group can readily copolymerize with other acrylate, methacrylate or acrylamide monomers to form an acrylamide-based copolymer according to Scheme I, above.

Other examples of useable linkers include, but are not limited to, any biocompatible linker can be used to conjugate a bioactive agent to the hydrophilic group on a monomer forming the poly(HPMA)-based polymer or on the poly(HPMA)-based polymer itself. In some embodiments, the linker can be any linker having about 40 atoms or less. In some embodiments, the linker can include poly(ethylene glycol) (PEG), poly(alkylene oxide), C1-C12 short chain alkyl, C1-C12 short chain cycloalkyl, C1-C12 aryl, peptide, protein, oligomer of amino acids or combinations thereof. In some embodiments, the linker is a labile linker. For example, such labile linkers can include, e.g., a peptide sequence such as glycine-phenylalinine-leucine-glycine. Some other labile linkers include, but are not limited to, succinic anhydride, glutaric anhydride, dimethyl succinic anhydride, methyl glutaric anhydride, thioesters, disulfide bonds, PLA-, PLGA-, PCL-oligomers and other ester and anhydride linkages.

Conjugation of Bioactive Agents

Any bioactive agent can be conjugated to the acrylamide-based copolymer. Conjugation can be achieved by binding force of any nature, e.g., hydrogen bonding, ionic interaction (e.g., ion pairs), interpenetrating network, or covalent chemical bonding. Preferably, the binding force between the bioactive agent and the acrylamide-based copolymer is covalent chemical bonding.

Conjugation of the bioactive agent to the acrylamide-based copolymer by chemical bonding can be carried out using any established coupling chemistry. For example, where the acrylamide-based copolymer or a linker attached thereto bears hydrophilic groups such as hydroxyl, amino or carboxylic groups, coupling the bioactive group and the hydrophilic groups can be readily achieved using EDC chemistry (see, e.g., Olde Damink L. H., et al., Biomaterials. 17(8):765-73 (1996)). Some other examples of coupling the bioactive agent to the hydrophilic groups via chemical bonding are described in U.S. patent application Ser. No. 10/857,141, the teaching of which is incorporated hereto in its entirety by reference.

Coating Construct

The acrylamide-based copolymer described herein can be used with or without a bioactive agent conjugated thereto. In some embodiments, the acrylamide-based copolymer can be used as a matrix including a bioactive agent or a topcoat on an implantable device to control the release of the bioactive agent (e.g., a drug) from the implantable device. In some embodiments, the acrylamide-based copolymer can form a topcoat on an implantable device as surface functionalization of the implantable device. The acrylamide-based copolymer can include a bioactive agent permanently bound thereto, the bioactive agent imparting beneficial surface biological properties to the implantable device. The matrix or topcoat can further include a biocompatible polymer other than the acrylamide-based copolymer ("biocompatible polymer") described herein.

Release of the bioactive agent from the matrix or topcoat of the implantable device can proceed via several mechanisms, which vary according to the nature of the binding force between the bioactive agent and the acrylamide-based copolymer. For example, where the binding force between bioactive agent and the acrylamide-based copolymer is not covalent chemical bonding, the bioactive agent can diffuse out of the matrix or topcoat so as to release into the blood stream or a tissue of a human being who receives an implantable device having a matrix or topcoat described herein. Where the nature of binding between a bioactive agent and the acrylamide-based copolymer is covalent bonding via a labile linker, release of the bioactive agent can be achieved by degradation or disruption of the labile linker to cause the bioactive agent to release into the blood stream or a tissue of a human being who receives an implantable device having a matrix or topcoat described herein. Degradation or disruption of the labile linker can be achieved by enzymedic degradation or hydrolytic degradation of the labile linker.

Biocompatible Polymers

The acrylamide-based copolymer described herein can be used with other biocompatible polymers. The biocompatible polymer can be biodegradable (either bioerodable or bioabsorbable or both) or nondegradable and can be hydrophilic or hydrophobic. Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly (3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly (ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly (methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(etheresters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), molecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof. Some examples of elastin protein mimetics include $(LGGVG)_n$, $(VPGVG)_n$, Val-Pro-Gly-Val-Gly, or synthetic biomimetic poly(L-glytanmate)-b-poly(2-acryloyloxyethyllactoside)-b-poly(1-glutamate) triblock copolymer. Note, the term "mimetic" can be used interchangeably with the term "mimic."

In some embodiments, the polymer can be poly(ethylene-co-vinyl alcohol), poly(methoxyethyl methacrylate), poly(dihydroxylpropyl methacrylate), polymethacrylamide, aliphatic polyurethane, aromatic polyurethane, nitrocellulose, poly(ester amide benzyl), co-poly-{[N,N'-sebacoyl-bis-(L-leucine)-1,6-hexylene diester]$_{0.75}$-[N,N'-sebacoyl-L-lysine benzyl ester]$_{0.25}$} (PEA-Bz), co-poly-{[N,N'-sebacoyl-bis-(L-leucine)-1,6-hexylene diester]$_{0.75}$-[N,N'-sebacoyl-L-lysine-4-amino-TEMPO amide]$_{0.25}$} (PEA-TEMPO), aliphatic polyester, aromatic polyester, fluorinated polymers such as poly(vinylidene fluoride-co-hexafluoropropylene), poly(vinylidene fluoride) (PVDF), and Teflon™ (polytetrafluoroethylene), a biopolymer such as elastin mimetic protein polymer, star or hyper-branched SIBS (styrene-block-isobutylene-block-styrene), or combinations thereof. In some embodiments, where the polymer is a copolymer, it can be a block copolymer that can be, e.g., di-, tri-, tetra-, or oligo-block copolymers or a random copolymer. In some embodiments, the polymer can also be branched polymers such as star polymers.

In some embodiments, a coating having the features described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

Bioactive Agents

Bioactive agents that can form a conjugation with the acrylamide-based copolymer described herein can include one or more bioactive agent(s), which can be therapeutic, prophylactic, or diagnostic agent(s). These agents can have anti-proliferative or anti-inflammatory properties or can have other properties such as antineoplastic, antiplatelet, anti-coagulant, anti-fibrin, antithrombogenic, antimitotic, antibiotic, antiallergic, antifibrotic, and antioxidant. The agents can be cystostatic agents, agents that promote the healing of the endothelium such as NO releasing or generating agents, agents that attract endothelial progenitor cells, agents that promote the attachment, migration or proliferation of endothelial cells (e.g., natriuretic peptides such as CNP, ANP or BNP peptide or an RGD or cRGD peptide), while impeding smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides, small interfering RNA (siRNA), small hairpin RNA (shRNA), aptamers, ribozymes and retroviral vectors for use in gene therapy. Examples of anti-proliferative agents include rapamycin and its functional or structural derivatives, 40-O-(2-hydroxy) ethyl-rapamycin (everolimus), and its functional or structural derivatives, paclitaxel and its functional and structural derivatives, as well as halofuginone which also has anti-fibrotic activity. Examples of rapamycin derivatives include 40-epi-(N1-tetrazolyl)-rapamycin (ABT-578), 40-O-(3-hydroxy) propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, mometasone, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which can be appropriate include alpha-interferon, pimecrolimus, imatinib mesylate, midostaurin, bioactive RGD, SIKVAV peptides, elevating agents such as cANP or cGMP peptides, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than non-therapeutic levels. The dosage or concentration of the bioactive agent can depend upon factors such as the particular circumstances of the patient, the nature of the trauma, the nature of the therapy desired, the time over which the administered ingredient resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device can be any suitable medical substrate that can be implanted in a human or veterinary patient. Examples of such implantable devices include self-expandable stents, balloon-expandable stents, stent-grafts, grafts (e.g., aortic grafts), heart valve prostheses, cerebrospinal fluid shunts, electrodes, pacemaker electrodes, catheters, sensors, endocardial leads (e.g., FINELINE and ENDOTAK, available from Guidant Corporation, Santa Clara, Calif.), anastomotic devices and connectors, orthopedic implants such as screws, spinal implants, and electrostimulatory devices. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP2ON," ELASTINITE (Nitinol), tantalum, nickel-titanium alloy, platinum-iridium alloy, gold, magnesium, or combinations thereof. "MP35N" and "MP2ON" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers or bioabsorbable metals such as magnesium could also be used with the embodiments of the present invention. In some embodiments, the device is a bioabsorbable stent.

Method of Use

In accordance with embodiments of the invention, an implantable device having a coating that includes the acrylamide-based copolymer described herein can be used for treating, preventing or ameliorating a medical condition. Preferably, the implantable device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents can be placed in a wide array of blood vessels, both arteries and veins. In some embodiments, the device described herein can be in dialysis, as grafts, or fistulae.

Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described features can then be expanded at the desired area of treatment. A post-insertion angiogram can also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable device comprising a coating, the coating comprising a conjugate of:
   a bioactive agent;
   a linker comprising poly(ethylene glycol) (PEG), poly(alkylene oxide), C1-C12 alkyl, C3-C12 cycloalkyl, C3-12 aryl, a peptide, a peptide sequence, a protein, an oligomer of amino acids, succinic anhydride, glutaric anhydride, dimethyl succinic anhydride, methyl glutaric anhydride, a thioester, a disulfide bond, a polylactic acid oligomer, a poly(lactic-co-glycolic acid) oligomer, Polycaprolactone oligomer, an ester linkage, or an anhydride linkage; and
   a copolymer of Formula II:

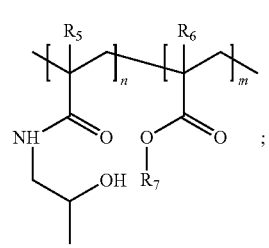

Formula II wherein $R_5$ and $R_6$ are independently $CH_3$ or H;
wherein $R_7$ is a straight or branched $C_1$-$C_{12}$ alkyl, aryl, cycloalkyl, or heterocyclic group;
wherein n and m are independently mole ratios from about 0.01 to about 0.99, with a proviso that n+m=1; and
wherein the linker conjugates the bioactive agent to the copolymer.

2. The implantable device of claim 1, wherein the linker comprises succinic anhydride, glutaric anhydride, dimethyl succinic anhydride, methyl glutaric anhydride, a thioester, a disulfide bond, a polylactic acid oligomer, a poly(lactic-co-glycolic acid) oligomer, a Polycaprolactone oligomer, an ester linkage, or an anhydride linkage.

3. The implantable device of claim 1, wherein the linker comprises succinic anhydride, glutaric anhydride, dimethyl succinic anhydride, or methyl glutaric anhydride.

4. The implantable device of claim 1, wherein the linker comprises poly(ethylene glycol) (PEG), a C1-C12 alkyl chain, or a peptide sequence.

5. The implantable device of claim 4, wherein the peptide sequence comprises glycine-phenylalinine-leucine-glycine.

6. The implantable device of claim 1, wherein the linker comprises poly(ethylene glycol) (PEG), poly(alkylene oxide), C1-C12 alkyl, C3-C12 cycloalkyl, or C3-C12 aryl.

7. The implantable device of claim 1, wherein the copolymer is poly[N-(2-hydroxypropyl)methacrylamide-co-methoxyethyl methacrylate] (HPMA-co-MOEMA).

8. The implantable device of claim 1, wherein the copolymer is a random or block copolymer.

9. The implantable device of claim 1, which is a stent.

10. The implantable device of claim 1, wherein the bioactive agent is selected from the group consisting of halofuginone, paclitaxel, docetaxel, estradiol, 17-beta-estradiol, a nitric oxide donor, super oxide dismutase, a super oxide dismutase mimic, 4-amino-2,2,6,6-tetramethylpiperidine-1-oxyl (4-amino-TEMPO), tacrolimus, dexamethasone, rapamycin, a rapamycin derivative, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N-1-tetrazolyl)-rapamycin (ABT-578), γ-hiridun, clobetasol, mometasone, pimecrolimus, imatinib mesylate, or midostaurin, or a prodrug, co-drug, or combination of these.

11. The implantable device of claim 9, wherein the bioactive agent is selected from the group consisting of halofuginone, paclitaxel, docetaxel, estradiol, 17-beta-estradiol, a nitric oxide donor, super oxide dismutase, a super oxide dismutase mimic, 4-amino-2,2,6,6-tetramethylpiperidine-1-oxyl (4-amino-TEMPO), tacrolimus, dexamethasone, rapamycin, a rapamycin derivative, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin, or a prodrug, co-drug, or combination of these.

12. The implantable device of claim 1, wherein the coating comprises a layer of matrix comprising the copolymer, linker and the bioactive agent.

13. The implantable device of claim 1, wherein the coating comprises a topcoat comprising the copolymer, linker and the bioactive agent.

14. The implantable device of claim 1, wherein the coating further comprises one or more biocompatible polymers selected from the group consisting of poly(ester amide), polyhydroxyalkanoates (PHA), poly(lactide-co-caprolactone), poly(glycolide-co-caprolactone), poly(tyrosine carbonates), poly(tyrosine ester), polyphosphoester, polyphosphoester urethane, polycyanoacrylates, poly(iminocarbonate), polyurethanes, silicones, polyesters, polyolefins, polyisobutylene and ethylene-alphaolefin copolymers, acrylic polymers and copolymers, polyvinyl chloride, polyvinyl ethers, polyvinyl methyl ether, polyvinylidene halides, polyacrylonitrile, polyvinyl ketones, polystyrene, polyvinyl esters, ethylene-methyl methacrylate copolymers, acrylonitrile-styrene copolymers, polyamides, polycaprolactam, polycarbonates, polyimides, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, poly(propylene oxide), poly(aspirin), 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), methacrylic acid (MA), acrylic acid (AA), alkoxymethacrylate, alkoxyacrylate, 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), polypropylene oxide-co-polyethylene glycol, poly(tetramethylene glycol), hydroxy functional poly(vinyl pyrrolidone), fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, and alginate.

15. The implantable device of claim 14, wherein the one or more biocompatible polymers are selected from the group consisting of poly(3-hydroxyalkanoates), poly(4-hydroxyalkanoates), vinyl halide polymers and copolymers, polyvinyl ethers, polyvinylidene halides, polyvinyl ketones, polyvinyl aromatics, polyamides and polyvinyl esters.

16. The implantable device of claim 14, wherein the one or more biocompatible polymers are selected from the group consisting of poly(3-hydroxypropanoate), poly(3-hydroxybutyrate), poly(3-hydroxyvalerate), poly(3-hydroxyhexanoate), poly(3-hydroxyheptanoate), poly(3-hydroxyoctanoate), poly(4-hydroxybutyrate), poly(4-hydroxyvalerate), poly(4-hydroxyhexanote), poly(4-hydroxyheptanoate), poly(4-hydroxyoctanoate), hydroxyethyl methacrylate (HEMA), hydroxypropyl methacrylate (HPMA), hydroxypropylmethacrylamide, PEG acrylate (PEGA), PEG-methacrylate, 2-methacryloyloxyethylphosphorylcholine (MPC), n-vinyl pyrrolidone (VP), polyvinyl chloride, polyvinyl methyl ether, polyvinylidene chloride, polyacrylonitrile, polystyrene, polycaprolactam and polyvinyl acetate.

17. A method of treating or ameliorating a medical condition, comprising implanting into a blood vessel the implantable device of claim 9.

18. A method of forming a coating on an implantable device, comprising:
providing a copolymer of Formula II:

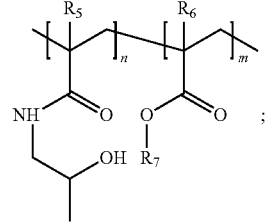

Formula II providing a bioactive agent;
providing a linker;
conjugating the bioactive agent to the copolymer with the linker; and
forming a coating comprising the conjugate on the implantable device;
wherein $R_5$ and $R_6$ are independently $CH_3$ or H;
wherein $R_7$ is a straight or branched $C_1$-$C_{12}$ alkyl, aryl, cycloalkyl, or heterocyclic group;
wherein n and m are independently mole ratios from about 0.01 to about 0.99, with a proviso that n+m=1; and
wherein the linker comprises poly(ethylene glycol) (PEG), poly(alkylene oxide), C1-C12 alkyl, C3-C12 cycloalkyl, C3-C12 aryl, a peptide, a protein, an oligomer of amino acids, succinic anhydride, glutaric anhydride, dimethyl succinic anhydride, methyl glutaric anhydride, a thioester, a disulfide bond, a poly-lactic acid oligomer, a poly(lactic-co-glycolic acid) oligomer, a Polycaprolactone oligomer, an ester linkage, or an anhydride linkage.

19. The method of claim 18, wherein the linker comprises succinic anhydride, glutaric anhydride, dimethyl succinic anhydride, methyl glutaric anhydride, a thioester, a disulfide bond, a polylactic acid oligomer, a poly(lactic-co-glycolic acid) oligomer, a Polycaprolactone oligomer, an ester linkage, or an anhydride linkage.

20. The method of claim 18, wherein the linker comprises succinic anhydride, glutaric anhydride, dimethyl succinic anhydride, or methyl glutaric anhydride.

21. The method of claim 18, wherein the linker comprises poly(ethylene glycol) (PEG), an alkyl chain, or a peptide sequence.

22. The method of claim 21, wherein the peptide sequence comprises glycine-phenylalinine-leucine-glycine.

23. The method of claim 18, wherein the linker comprises poly(ethylene glycol) (PEG), poly(alkylene oxide), C1-C12 alkyl, C3-C12 cycloalkyl, or C3-C12 aryl.

24. The method of claim 18, wherein the coating further comprises one or more biocompatible polymers selected from the group consisting of poly(ester amide), polyhydroxyalkanoates (PHA), poly(lactide-co-caprolactone), poly(glycolide-co-caprolactone), poly(tyrosine carbonates), poly(tyrosine ester), polyphosphoester, polyphosphoester urethane, polycyanoacrylates, poly(iminocarbonate), polyurethanes, silicones, polyesters, polyolefins, polyisobutylene and ethylene-alphaolefin copolymers, acrylic polymers and copolymers, polyvinyl chloride, polyvinyl ethers, polyvinyl methyl ether, polyvinylidene halides, polyacrylonitrile, polyvinyl ketones, polystyrene, polyvinyl esters, ethylene-methyl methacrylate copolymers, acrylonitrile-styrene copolymers, polyamides, polycaprolactam, polycarbonates, polyimides, poly(glyceryl sebacate), poly(propylene fumarate), poly(n-butyl methacrylate), poly(sec-butyl methacrylate), poly (isobutyl methacrylate), poly(tert-butyl methacrylate), poly (n-propyl methacrylate), poly(isopropyl methacrylate), poly (ethyl methacrylate), poly(methyl methacrylate), polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, poly(propylene oxide), poly(aspirin), 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), methacrylic acid (MA), acrylic acid (AA), alkoxymethacrylate, alkoxyacrylate, 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), polypropylene oxide-co-polyethylene glycol, poly(tetramethylene glycol), hydroxy functional poly(vinyl pyrrolidone), fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, and alginate.

25. The method of claim 24, wherein the one or more biocompatible polymers are selected from the group consisting of poly(3-hydroxyalkanoates), poly(4-hydroxyalkanaotes), vinyl halide polymers and copolymers, polyvinyl ethers, polyvinylidene halides, polyvinyl ketones, polyvinyl aromatics, polyamides and polyvinyl esters.

26. The method of claim 24, wherein the one or more biocompatible polymers are selected from the group consisting of poly(3-hydroxypropanoate), poly(3-hydroxybutyrate), poly(3-hydroxyvalerate), poly(3-hydroxyhexanoate), poly (3-hydroxyheptanoate), poly(3-hydroxyoctanoate), poly(4-hydroxybutyrate), poly(4-hydroxyvalerate), poly(4-hydroxyhexanote), poly(4-hydroxyheptanoate), poly(4-hydroxyoctanoate), hydroxyethyl methacrylate (HEMA), hydroxypropyl methacrylate (HPMA), hydroxypropylmethacrylamide, PEG acrylate (PEGA), PEG-methacrylate, 2-methacryloyloxyethylphosphorylcholine (MPC), n-vinyl pyrrolidone (VP), polyvinyl chloride, polyvinyl methyl ether, polyvinylidene chloride, polyacrylonitrile, polystyrene, polycaprolactam and polyvinyl acetate.

* * * * *